US012036216B2

(12) United States Patent
Lu et al.

(10) Patent No.: US 12,036,216 B2
(45) Date of Patent: Jul. 16, 2024

(54) APIXABAN FILM PRODUCT AND USES THEREOF (71) Applicant: TAHO Pharmaceuticals Ltd., Taipei (TW)

(72) Inventors: Tachien Lu, New Taipei (TW); Catherine Lee, Happy Valley, OR (US)

(73) Assignee: TAHO Pharmaceuticals Ltd., Taipei (TW)

( * ) Notice: Subject to any disclaimer, the term of this patent is extended or adjusted under 35 U.S.C. 154(b) by 0 days.

(21) Appl. No.: 17/832,210

(22) Filed: Jun. 3, 2022

(65) Prior Publication Data

US 2022/0387415 A1 Dec. 8, 2022

Related U.S. Application Data (60) Provisional application No. 63/208,134, filed on Jun. 8, 2021.

(51) Int. Cl.
| A61K 31/4545 | (2006.01) |
| A61K 9/00 | (2006.01) |
| A61K 9/70 | (2006.01) |
| A61K 45/06 | (2006.01) |
| A61K 47/02 | (2006.01) |
| A61K 47/10 | (2017.01) |
| A61K 47/26 | (2006.01) |
| A61K 47/38 | (2006.01) |

(52) U.S. Cl.
CPC .......... *A61K 31/4545* (2013.01); *A61K 9/006* (2013.01); *A61K 9/7007* (2013.01); *A61K 45/06* (2013.01); *A61K 47/02* (2013.01); *A61K 47/10* (2013.01); *A61K 47/26* (2013.01); *A61K 47/38* (2013.01)

(58) Field of Classification Search
CPC .. A61K 31/4545; A61K 9/006; A61K 9/7007; A61K 45/06; A61K 47/02; A61K 47/10; A61K 47/26; A61K 47/38
See application file for complete search history.

(56) References Cited

U.S. PATENT DOCUMENTS

| 9,326,945 | B2 * | 5/2016 | Patel .................... A61K 9/2018 |
| 10,709,662 | B1 * | 7/2020 | Ahmed ................ A61K 9/1075 |
| 2015/0272891 | A1 | 10/2015 | Meergans et al. |
| 2017/0202826 | A1 | 7/2017 | Nause |

(Continued)

FOREIGN PATENT DOCUMENTS

| CA | 2765413 A1 * | 12/2010 | ........... A61K 31/437 |
| TW | 202106297 A | 2/2021 | |
| WO | 2020/127819 A2 | 6/2020 | |

OTHER PUBLICATIONS

International Search Report and Written Opinion for corresponding International Application No. PCT/US2022/32111, dated Aug. 18, 2022.

(Continued)

*Primary Examiner* — Savitha M Rao
*Assistant Examiner* — Andrew P Lee
(74) *Attorney, Agent, or Firm* — Leason Ellis LLP (57) ABSTRACT The present disclosure provides an apixaban film product for treatment and prevention of thrombosis and related disorders. Also provided is a method of making the film product. The film product comprises an anticoagulant and a hydrophilic cellulosic polymer.

10 Claims, 3 Drawing Sheets

(56) References Cited

U.S. PATENT DOCUMENTS

2020/0009125 A1 1/2020 Huang et al.
2020/0338012 A1 10/2020 Lee et al.

OTHER PUBLICATIONS

Berge et al., "Pharmaceutical Salts", 1977, Journal of Pharmaceutical Sciences, vol. 66:1-19.
T. Higuchi and W. Stella, "Pro-drugs as Novel Delivery Systems", Sep. 10, 1974, vol. 14 of the A.C.S. Symposium Series.
Office Action for corresponding Taiwan Application No. 111121267, dated Mar. 22, 2023.
International Preliminary Report on Patentability in PCT Application No. PCT/US2022/032111, mailed Nov. 21, 2023 (6 pages).

* cited by examiner

FIG. 3

APIXABAN FILM PRODUCT AND USES THEREOF

CROSS REFERENCE TO RELATED PATENT APPLICATIONS

This application claims priority to U.S. Provisional Application No. 63/208,134 filed on Jun. 8, 2021, which is incorporated by reference in its entirety.

1. FIELD

The present disclosure provides an apixaban film product for treatment and prevention of thrombosis and related disorders. Also provided is a method of making the film product. The film product comprises an anticoagulant and a hydrophilic cellulosic polymer.

2. BACKGROUND

A stroke is a sudden neurological deficit of vascular origin lasting more than 24 hours or associated with infarction on brain imaging. Stroke remains a major source of morbidity and mortality in the USA. On average, someone died of stroke every 3 minutes 33 seconds in 2016. In 2018, stroke accounted for about 1 of every 19 deaths in the US and the age-adjusted stroke death rate was 37.1 per 100,000, a decrease of 11.9% from 2008, whereas the actual number of stroke deaths increased 10.2% during the same time period (AHA Heart Disease and Stroke Statistics-2021 Update). About 15% of all strokes are attributable to atrial fibrillation (AF). It is affecting up to 2% of the general population in the developed world, and it is associated with a five fold risk of stroke and a threefold incidence of congestive heart failure. Patients on dialysis with AF have significantly higher 1-year mortality rates compared with those without (hazard ratio [HR], 1.72 after adjustment for age, sex, and race; 95% confidence interval [95% CI], 1.70 to 1.73). Patients on dialysis are also at increased risk of ischemic or haemorrhagic stroke compared with the general population (age-adjusted relative risk, 6.1; 95% CI, 5.1 to 7.1).

Post-stroke dysphagia (PSD), defined here as difficulty in swallowing after a stroke, is a common complication affecting many patients in the first few hours and days after ictus. PSD is associated with increased mortality and morbidity due in part to aspiration, pneumonia, and malnutrition. Although many stroke patients recover swallowing spontaneously, 11-50% still have dysphagia at six months. Persistent dysphagia independently predicts poor outcome and institutionalization. Dysphagia leading to aspiration of ingested foods, liquids, or oral secretions, is thought to be the primary risk factor for pneumonia after stroke. Dysphagic patients are three times, and those with confirmed aspiration eleven times, more likely to develop pneumonia.

Apixaban is one of the most upstream anti-thrombotic drug that blocks the conversion of prothrombin to thrombin. Fibrinogen in an environment with reduced thrombin will be converted less to fibrin for clot formation. Apixaban when administered orally, though safer than warfarin, still causes gastrointestinal ("GI") track, including upper GI, lower GI and rectal bleeding. Oral administration of apixaban is, however, sometimes undesirable. Apixaban is a poor candidate for traditional oral delivery. Providing an apixaban transdermal system faces many technology barrier because of its physicochemical properties. With a water solubility of 0.0679 mg/ml, melting point of 237-238° C., polar surface area of 110.76 Å$^2$, it has been a huge hurdle to provide an effective oral film comprising Apixaban. It is therefore, important to provide an oral film that are tailored for apixaban delivery taking into consideration of its physicochemical properties.

Sometimes a patient may have difficulty swallowing pills, or remembering to take the oral doses at all. Patient compliance has been a concern for treatments such as thrombosis. Since thrombosis does not cause symptoms until it is too late. Thus, it is desirable to have an apixaban oral film that can continually deliver apixaban over an extended period of time. For delivery to humans, better designs to improve apixaban permeation will be required. Thus, an oral apixaban delivery film with adequate drug loading and sufficient flux is needed for effective therapy of ailments such as hypertension or prophylaxis of migraine. There is a need for improved delivery of apixaban, especially sustained oral delivery over a period of time.

Apixaban is well absorbed in rat, dog, and chimpanzee, with absolute oral bioavailability of approximately 50% or greater. The steady-state volume of distribution ($V_d$) of apixaban is approximately 0.5, 0.2, and 0.17 L/kg in rats, dogs, and chimpanzees, while clearance (CL) is approximately 0.9, 0.04, and 0.018 L/h/kg, respectively. In vitro metabolic clearance of apixaban is also low. Renal clearance comprises approximately 10-30% of systemic clearance in rat, dog, and chimpanzee. Anti-FXa activity, prothrombin time (PT), and HEPTEST® clotting time (HCT) prolongation correlated well with plasma apixaban concentration in rat, dog and chimpanzee. There was no lag time between apixaban plasma concentration and the pharmacodynamics (PD) markers, suggesting a rapid onset of action of apixaban. The $IC_{50}$ values for anti-factor Xa activity were 0.73±0.03 and 1.5±0.15 µM for rat and dog, respectively. The apparent Ki values for PT were approximately 1.7, 6.6, and 4.8 µM for rat, dog and chimpanzee, respectively.

According to the studies performed on the ELIQUIS®, the overall preclinical data showed no hazards for humans when conducting studies of safety pharmacology, repeat-dose toxicity, genotoxicity, carcinogenicity, fertility, and embryo-fetal fertility. The pharmacodynamic study revealed that action of apixaban in the repeat-dose toxicity studies had the most effects on blood coagulation parameters. The toxicity studies also demonstrated little to no increase of bleeding tendency.

Apixaban is an immediate release tablet formulation with rapid dissolution (at least 80% dissolved within 30 minutes) and pH-independent aqueous solubility. Apixaban has predictable pharmacokinetic (PK) properties, and exposure is dose proportional for the approved dose range of 2.5-10 mg. The bioavailability of apixaban is approximately 50%, and it is absorbed primarily in the upper gastrointestinal (GI) tract, proximal to the colon. Peak apixaban plasma concentration is reached approximately 3 hours after oral administration in healthy adults, with a mean elimination $t_{1/2}$ of approximately 12 hours. Elimination occurs via multiple pathways, including metabolism, renal elimination of unchanged drug, and excretion into the intestinal tract. In addition to having a pharmacologic profile consistent with twice-daily dosing, there is limited potential for drug-drug or drug-food interactions.

Certain patients, such as elderly individuals, young children, and some hospitalized patients, may be unable to swallow solid dosage forms. Pediatric patients<6 years of age may have difficulty swallowing adult dosage forms, and dysphagia is also a common potential complication of treatment in elderly patients. Patients with difficulty swal- lowing medication are more likely to delay or skip taking their medications entirely or seek alternate methods of administration. As a consequence, dysphagia is associated with a higher risk of medication errors.

In these patients, in the absence of alternative formulations, mixing capsule contents or crushed tablets with semi-solid foods or liquids is a common practice. However, extemporary manipulations of solid oral dose forms can alter the PK properties of the drug, and in some cases, relative bioavailability may be significantly affected. For example, the oral bioavailability of dabigatran etexilate mesylate increases by 75% when the pellets are taken without the capsule shell compared with the intact capsule formulation.

Therefore, it is important to develop a novel, oral film formulation of apixaban, that serves as an alternative for patients who have difficulty swallowing a whole tablet or crushed tablets due to advanced age or post stroke dysphagia. Additional benefits include, ensuring that patients take their medication over a period time to reduce the risk of stroke and systemic embolism, less plasma concentration variations and potentially reduce organ bleeding due to Apixaban anti-clotting properties.

3. SUMMARY

The present disclosure provides a film product comprising apixaban or a pharmaceutically acceptable salt thereof.

459.4971
$C_{25}H_{25}N_5O_4$

Provided herein is a water-soluble film product comprising:
(i) apixaban or a pharmaceutically acceptable salt thereof; and (ii) a water-soluble polymer comprising a hydrophilic cellulosic polymer wherein:

(i) the water-soluble polymer comprises at least 10% hydrophilic cellulosic polymer, and in certain embodiments, less than 5% of polyethylene oxide, (ii) less than 77 wt % of apixaban or a pharmaceutically acceptable salt thereof dissolves within 30 minutes in a pH 6.8 phosphate buffer containing 0.05% sodium lauryl sulfate, (iii) the film comprises less than 10% of water content, and (iv) the disintegration time of the film is less than 5 minutes.

In one embodiment, the apixaban is crystalline.
In one embodiment, less than 77% of apixaban dissolves within 30 minutes in a pH 6.8 phosphate buffer containing 0.05% sodium lauryl sulfate.
In one embodiment, the water-soluble film comprises 8-12% wt/wt % of apixaban.
In one embodiment, the water-soluble film comprises 10% wt/wt % of apixaban.
In one embodiment, the hydrophilic cellulosic polymer is HPMC or carboxymethyl cellulose ("CMC") polymer.
In one embodiment, the HPMC is HPMC 3, HPMC E5, HPMC E6, HPMC E15, HPMC E50, HPMC 5FM, HPMC E10M, HPMC K 250 PH, HPMC K 750 PH, HPMC K1500PH, HPMC K4M, HPMC K15M K35M, HPMC K100M, HPMC K200M or a combination thereof.
In one embodiment, the film comprises lower molecular weight of HPMC in combination with Eudragit polymer and Carbomer.
In one embodiment, the water-soluble film further comprises PEG, maltose, starch, glycerin, water soluble resins, or a combination thereof.
In one embodiment, the PEG is PEG 6000.
In one embodiment, the film has a bulk material viscosity of 10,000 cps to 100,000 cps
In one embodiment, the film has a thickness of 2 mils to 9 mils.
In one embodiment, the film has a thickness of 3 mils to 9 mils.
In one embodiment, the water-soluble film further comprises an additional pharmaceutical active ingredient.
In one embodiment, the water-soluble film further comprises one or more sweeteners.
In one embodiment, the water-soluble film further comprises one or more flavors.
In one embodiment, the water-soluble film further comprises an anticoagulant.

Provided herein is a method for treating thrombosis or a related disorder comprising the step of applying the film product to a human subject in need thereof.
In one embodiment, about 0.5 mg to about 20 mg of apixaban is delivered from the film product to the human subject.
In one embodiment, the film product is stable in room temperature for more than 1 month with less than 5% impurities.

In certain embodiments, the film product comprises apixaban (free base). In certain embodiments, the film product comprises an ester of apixaban. In one embodiment, the film product comprises an apixaban salt. In certain embodiments, the film product is an oral film.

Provided herein is a film product that delivers apixaban base or a salt thereof in a therapeutically effective amount. In certain embodiment, the film product delivers doses of 0.5 mg, 1 mg, 2.5 mg, 5 mg, 10 mg, 15 mg, 20 mg, and 40 mgapixaban free base equivalent per day (adjusted for free base form and oral bioavailability). The formulations have low irritation potential and contain sufficient drug to support one-day or multi-day delivery and rapidly dissolves in the oral cavity.

In one aspect, an oral apixaban delivery film is provided to provide health benefit to a subject in need thereof. The film product is flexible, self-supporting and provides a uniform distribution of the components within the film. The film product comprises a water-soluble polymer which comprises at least 10% hydrophilic cellulosic polymer and no more than 5% polyethylene oxide. In certain embodiments, the film product comprises 0-2%, 2-3%, 3-4%, 4-5%, 5-6%, 6-7% of polyethylene oxide. The film product contains an amount of apixaban or a pharmaceutically acceptable salt thereof sufficient for a rate-control delivery. The film product has no more than about 80 wt % of apixaban dissolves within about 30 minutes in about a pH 6.8 phosphate buffer containing about 0.05% sodium lauryl sulfate. In certain embodiments, the film product has about 60-70 wt %, 70-80 wt % of apixaban dissolves within about 30 minutes in about a pH 6.8 phosphate buffer containing about 0.05% sodium lauryl sulfate. The film product contains no more than 10% water and the disintegration time of the film is less than 5 minutes. In certain embodiments, the film product contains about 1-3%, 3-5%, 5-7%, 7-10% water. In certain embodiments, the film product disintegrates in about 1-2 minutes, 2-4 minutes, 4-5 minutes, 5-10 minutes, 10-15 minutes, 15-20 minutes, 20-30 minutes. In one embodiment, the apixaban drug is apixaban free base.

In another aspect, provided herein is a method of making an apixaban film product. In one aspect, provided herein is a method of using the apixaban film product.

In one embodiment, an oral film is provided with an effective amount of apixaban. In one embodiment, the apixaban is completely dissolved into the oral film. Once applied to a subject's oral cavity, the film disintegrates in less than 30 minutes.

In one embodiment, the oral film delivery of apixaban results in lower adverse events than with other oral delivery. Further, the present oral film allows a more steady sustained delivery than doses other formulations taken orally at time intervals hours apart. The oral film leads to improved compliance in the patients.

In one embodiment, the oral delivery of a therapeutic dose of apixaban (about 0.25 mg to 30 mg per day) from a water-soluble thin, flexible oral film. In certain embodiments, the oral film is about 1 to 20 cm² in size. In one embodiment, the oral film is about 50 μm to 200 μm thick. In certain embodiment, the oral film delivers the drug for a duration of 4 hours to 24 hours after it is disintegrated in the oral cavity. In certain embodiments, the drug loading is 8%, and 10%.

In certain embodiments, the film product delivers 5 μg-20 mg of apixaban per dose. In one embodiment, the film product comprises a composition comprising apixaban. In certain embodiments, the film product delivers a composition comprising apixaban that has a half-life of 1-10 hours. In certain embodiments, the film delivers a composition comprising apixaban that has a melting point of about 237° C. In certain embodiments, the film product comprising apixaban has an aqueous solubility of less than 1 mg/ml.

The therapeutic dose requirement for film product administration has been determined by adjusting the prescribed oral dose of apixaban fumarate with the oral bioavailability and the molecular weight difference of the salt to that of the free base (which oral bioavailability and molecular weight difference are known to those skilled in the art).

In one aspect, certain film products are provided that can deliver apixaban base systemically at a therapeutically effective rate for providing therapeutic benefits for ailments without using a significant amount of, and even without any, permeation enhancer. In certain embodiments, rate-control is provided to slow down the flux by including a rate-control hydrophilic cellulosic polymer.

In one embodiment, a film product is applied to the oral cavity of a patient for use to render therapeutic benefits for ailments such as thrombosis. As used herein, "treatment" or "therapeutic benefit" includes relief or reduction of symptoms and prophylaxis of symptoms. In one embodiment, the apixaban film product is used for postoperative administration such as for prophylaxis to reduce the risk of thrombosis.

In another aspect, a method is provided to load a therapeutically effective amount of apixaban into the film product. Using film product would increase patient compliance and would reduce a caregiver's burden.

In one aspect, the present film product with apixaban will address some of the challenges to providing optimal apixaban therapy. The film product results in less gastrointestinal exposure and could decrease the incidence of gastrointestinal side effects associated with peripheral cholinergic stimulation. The film product provides a bioavailability and dissolution profile which produce gradually increasing plasma levels over time and may reduce the need for dosing titration and simplify the dosing regimen. An ability to achieve and tolerate higher apixaban levels or more rapid dose titration would be expected to result in greater efficacy, earlier onset of symptomatic improvement (for symptomatic ailments), or both.

In one embodiment, the one or more hydrophilic cellulosic polymers provides a solubility of no greater than about 20% for apixaban or a pharmaceutically acceptable salt thereof.

In one embodiment, the apixaban or a pharmaceutically acceptable salt thereof is in an amount ranging from about 2% to about 15% by weight (wt %) relative to total weight of the film product.

In one embodiment, the apixaban or a pharmaceutically acceptable salt thereof is in an amount ranging from about 5% to about 10% by weight (wt %) relative to total weight of the film product.

In one embodiment, the apixaban or a pharmaceutically acceptable salt thereof is about 8% by weight (wt %) relative to total weight of the film product.

Provided in the present disclosure is a method for treatment of deep vein thrombosis (DVT) and pulmonary embolism (PE), and prevention of recurrent DVT and PE, and prevention of venous thromboembolic events (VTE) comprising the step of administering a film product to a human subject in need thereof.

In certain embodiments, about 1 mg to about 3 mg, about 3 mg to about 5 mg, about 5 to about 10 mg, about 10 mg to 12 mg, about 12 mg to about 15 mg, about 15 mg to about 20 mg of apixaban is delivered from the film product to the human subject.

In one embodiment, about 0.5 mg to about 20 mg of apixaban is delivered from the film product to the human subject.

In one embodiment, the apixaban or a pharmaceutically acceptable salt thereof is in an amount ranging from about 2% to about 15% by weight (wt %) relative to total weight of the pharmaceutical composition.

In one embodiment, the apixaban or a pharmaceutically acceptable salt thereof is in an amount ranging from about 5% to about 10% by weight (wt %) relative to total weight of the pharmaceutical composition.

Figure 1:
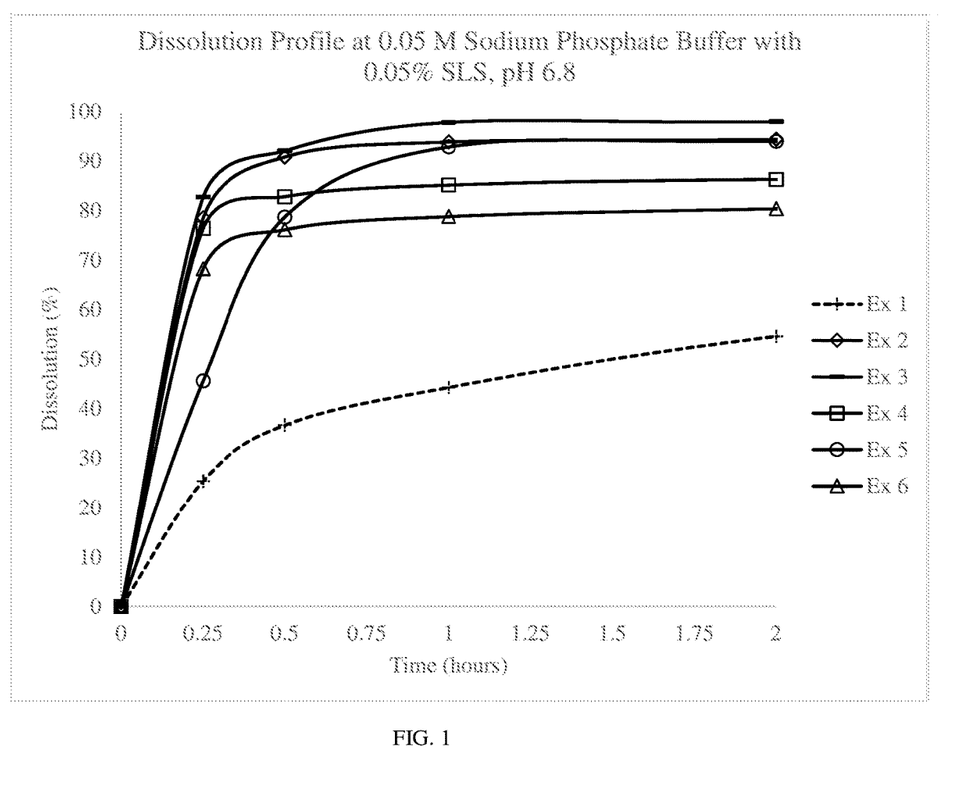
FIG. 1: Dissolution Profile of Polyethylene Oxide Effect, presence of polyethylene oxide apixaban would affect the release from the film.
Figure 2:
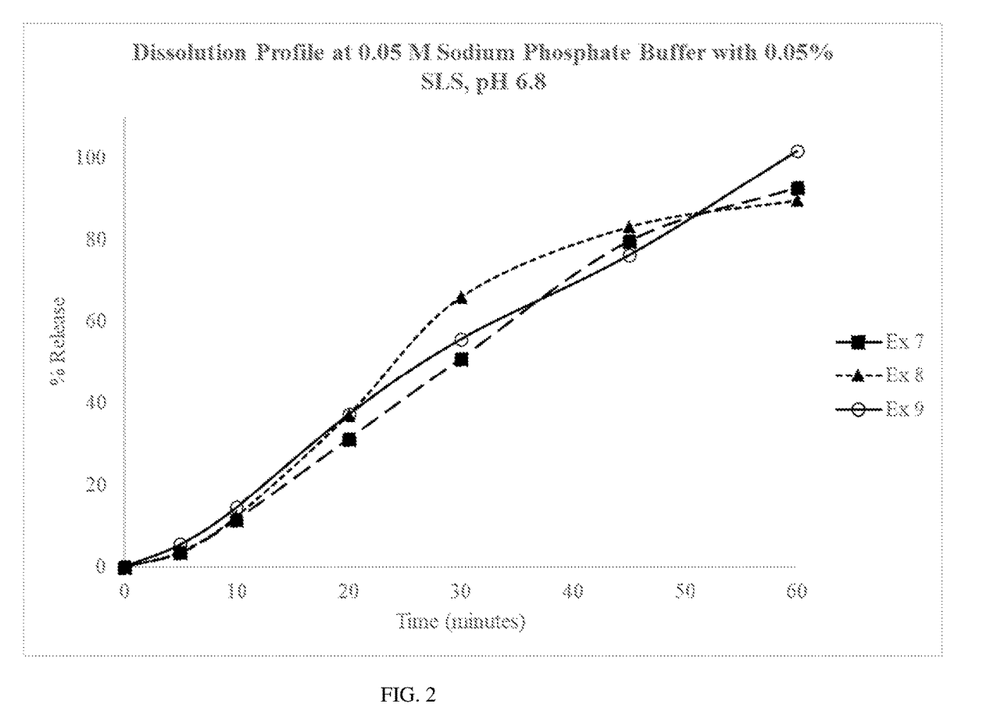
FIG. 2: Dissolution Profile of High Molecular Weight HPMC Effect, presence of higher molecular weight reduces the release of the apixaban from the film.
Figure 3:
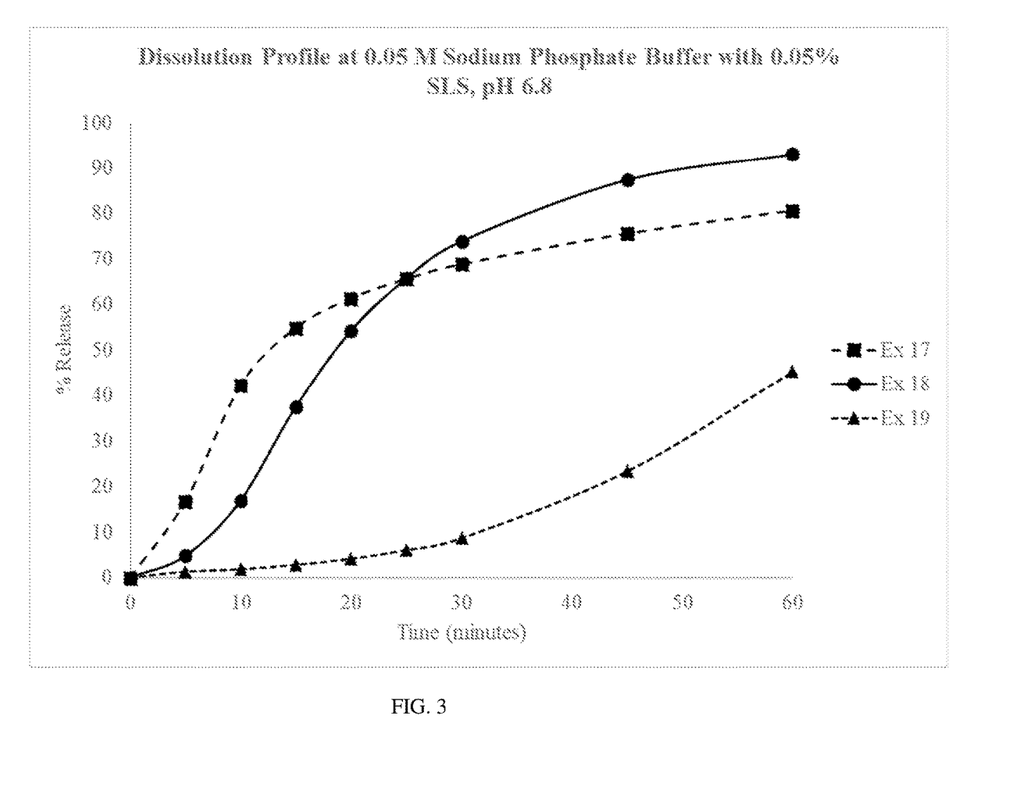
FIG. 3: Dissolution Profile of Low Molecular Weight HPMC with Eudragit Polymers, presence of Eudragit Polymers reduces the release of the apixaban from the film.

4.2 DEFINITIONS

As used herein, the singular forms "a", "an" and "the" include plural referents unless the context clearly indicates otherwise. Thus, for example, reference to "an ingredient" includes mixtures of ingredients, reference to "an active pharmaceutical agent" includes more than one active pharmaceutical agent, and the like.

The terms "active agent", "pharmacologically active agent" and "drug" are used interchangeably herein to refer to a chemical material or compound that includes a desired pharmacological, physiological effect and include agents that are therapeutically effective. The terms also encompass pharmaceutically acceptable, pharmacologically active derivatives and analogs of those active agents specifically mentioned herein, including, but not limited to, salts, esters, amides, prodrugs, active metabolites, inclusion complexes, enantiomers S(−) or R(+), analogs of the active agent (e.g., apixaban).

The pharmaceutically active agent of the present disclosure may be a salt. As used herein, a "salt" is a salt of the present compound which has been modified by making acid or base, salts of the compounds. The salt may be pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately treating a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

The present methods also encompass administering a physiologically functional derivative of the present compound. As used herein, the term "physiologically functional derivative" refers to a compound (e.g., a drug precursor) that is transformed in vivo to yield the present compound or its active metabolite, or a pharmaceutically acceptable salt, hydrate or solvate of the compound. The transformation may occur by various mechanisms (e.g., by metabolic or chemical processes), such as, for example, through hydrolysis. Prodrugs are such derivatives, and a discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

As used herein, the term "about" as a modifier to a quantity is intended to mean+ or −5% inclusive of the quantity being modified.

As used herein, "wt %", "% w/w" or "% (w/w)" refer to % by weight of the composition.

The present agent/composition may be administered therapeutically to achieve a therapeutic benefit ("treating") or prophylactically to achieve a prophylactic benefit ("preventing"). By therapeutic benefit is meant eradication or amelioration of the disorder or condition being treated, and/or eradication or amelioration of one or more of the symptoms associated with the disorder or condition. By prophylactic benefit is meant prevention or delay of the onset of the condition, and/or prevention or delay of the onset of one or more of the symptoms associated with the condition. In certain embodiments, an effective amount of the present agent/composition to be administered prevents the condition from developing or being exacerbated into more serious conditions.

"Treating" or "treatment" of a state, disorder or condition includes: (1) preventing or delaying the appearance of clinical symptoms of the state, disorder, or condition developing in a person who may be afflicted with or predisposed to the state, disorder or condition but does not yet experience or display clinical symptoms of the state, disorder or condition; or (2) inhibiting the state, disorder or condition, i.e., arresting, reducing or delaying the development of the disease or a relapse thereof (in case of maintenance treatment) or at least one clinical symptom, sign, or test, thereof; or (3) relieving the disease, i.e., causing regression of the state, disorder or condition or at least one of its clinical or sub-clinical symptoms or signs. The benefit to a subject to be treated is either statistically significant or at least perceptible to the patient or to the physician.

An effective amount of an agent/drug refers to a therapeutically effective amount or a prophylactically effective amount. A "prophylactically effective amount" refers to an amount effective, at dosages and for periods of time necessary, to achieve the desired prophylactic result. In certain embodiments, since a prophylactic dose is used in subjects prior to or at an earlier stage of a disorder, the prophylactically effective amount is less than the therapeutically effective amount. In certain embodiments, the prophylactically effective amount is similar to, identical to, or more than, the therapeutically effective amount. A therapeutically effective amount of a drug is an amount effective to demonstrate a desired activity of the drug. A therapeutically effective amount may vary depending on the compound, the disorder and its severity and the age, weight, physical condition and responsiveness of the subject to be treated. In certain embodiments, the drug-containing layer, or the reservoir layer or the present composition further comprises a pharmaceutically acceptable carrier, vehicle, excipient and/or diluent.

The term "film product" is intended to refer to a self-contained, discrete dosage form that, when administered to a subject for disintegration or dissolution to release the drug(s) for local and/or systemic absorption.

The term "oral film" is intended to refer to a self-contained, discrete dosage form that, when administered to a subject orally for disintegration or dissolution to release the drug(s) for local and/or systemic absorption. Some important characteristics of an oral film include flux rate, lag time and stability. Flux rate relates to the rate at which the oral film delivers apixaban. Lag time relates to the time required for apixaban blood concentration to reach steady state after application of the oral film. Lag time preferably matches apixaban metabolic rate in order to minimize fluctuations in blood concentration between applications of successive oral film. Lastly, stability relates to the amount of impurities that develops within the oral film while in storage.

5. DETAILED DESCRIPTION

The present disclosure provides a film product containing apixaban, or a pharmaceutically acceptable salt, derivative, or solvate thereof, as an active agent. In certain embodiments, the film product is for daily administration with minimal apixaban blood concentration fluctuations. In certain embodiments, the film product provides high flux of apixaban and low crystallization of the active agent.

The present disclosure also provides a film product containing apixaban, or a pharmaceutically acceptable salt, derivative, or solvate thereof, as an active agent. In one embodiment, the film comprises a hydrophilic cellulosic polymers polymer and polyethylene oxide. The films contain an active ingredient that is evenly distributed throughout the film. The even or uniform distribution is achieved by controlling one or more parameters, and particularly the elimination of air pockets prior to and during film formation and the use of a drying process that reduces aggregation or conglomeration of the components in the film as it forms into a solid structure.

The present disclosure provides methods and film products for treating or preventing thrombosis. In certain embodiments, the disclosure provides methods and compositions for treating or preventing left ventricular thrombus, atrial fibrillation, acute coronary syndrome, reduce the risk of stroke and systemic embolism. In one embodiment, the methods and film products provide treatment of subjects with nonvalvular atrial fibrillation. In certain embodiments, the methods and film products provide prophylaxis of deep vein thrombosis, which may lead to pulmonary embolism. In certain embodiments, the subject has undergone surgery. In certain embodiments, the methods and film products reduce the risk of recurrent deep vein thrombosis and pulmonary embolism following initial therapy.

Also encompassed by the present disclosure is a method of treating or preventing thrombosis and other disorders. The method may comprise administering the film product to a subject.

5.1 Films for the Delivery of Apixaban

In certain embodiments, film products are film formulations intended for delivery of apixaban and dissolve after delivery. In one embodiment, the present disclosure provides an apixaban oral dissolving film.

Apixaban, is a pyrazolopyridine that is 7-oxo-4,5,6,7-tetrahydro-1H-pyrazolo[3,4-c]pyridine-3-carboxamide substituted at position 1 by a 4-methoxyphenyl group and at position 6 by a 4-(2-oxopiperidin-1-yl)phenyl group with the following representative structure.

459.4971
$C_{25}H_{25}N_5O_4$

In certain embodiments, apixaban is in the free base form. In certain embodiments, the film product comprises a pharmaceutically acceptable salt of apixaban. In certain embodiments, the salt of apixaban is an acid addition salt formed by treatment with an appropriate acid, such as a hydrohalic acid, for example hydrochloric or hydrobromic acid, sulfuric acid, nitric acid, phosphoric acid, acetic acid, propanoic acid, hydroxyacetic acid, 2-hydroxypropanoic acid, 2-oxopropanoic acid, ethanedioic acid, propanedioic acid, butanedioic acid, (Z)-2-butenedioic acid, (E)-2-butenedioic acid, 2-hydroxybutanedioic acid, 2,3-dihydroxybutanedioic acid, 2-hydroxy-1,2,3-propanetricarboxylic acid, methanesulfonic acid, ethanesulfonic acid, benzenesulfonic acid, 4-methylbenzenesulfonic acid, cyclohexanesulfamic acid, 2-hydroxybenzoic acid or 4-amino-2-hydroxybenzoic acid. In one embodiment, the present film product comprises the apixaban base form.

In certain embodiments, the thin film comprises an ester of apixaban.

In certain embodiments, the apixaban or a pharmaceutically acceptable salt thereof is in an amount ranging from about 0.5-2%, from about 1-3%, 2% to about 15% by weight (wt %) relative to total weight of the thin film.

In certain embodiments, the apixaban or a pharmaceutically acceptable salt thereof is in an amount ranging from about 0.5-5%, from about 1-3%, from about 5% to 15% by weight (wt %) relative to total weight of the film product.

In certain embodiments, apixaban or its pharmaceutically acceptable salt thereof is in an amount ranging from about 0.1% to about 0.5% by weight (wt %), from about 0.5% to about 1% by weight (wt %), from about 1% to about 2% by weight (wt %), from about 2% to about 3% by weight (wt %), from about 3% to about 4% by weight (wt %), from about 4% to about 5% by weight (wt %), from about 5% to about 6% by weight (wt %), from about 6% to about 7% by weight (wt %), from about 7% to about 8% by weight (wt %), from about 8% to about 9% by weight (wt %), from about 9% to about 10% by weight (wt %), from about 10% to about 11% by weight (wt %), from about 11% to about 12% by weight (wt %), from about 12% to about 13% by weight (wt %), about 13% to about 14% by weight (wt %), about 14% to 15% by weight (wt %), about 15% to about 16% by weight (wt %), about 16% to 17% by weight (wt %), about 17% to 18% by weight (wt %), or about 18% to 19% by weight (wt %), or about 19% to 20% by weight (wt %), relative to the total weight of the film product.

The apixaban or salt thereof may be present in the film product in combination with another active pharmaceutical ingredient. Suitable active pharmaceutical ingredients for combination with apixaban would be known to those of skill in the art.

Oral thin films are thin films containing a pharmaceutically active ingredient which are placed directly in the oral cavity or are placed against the oral mucosa and dissolve there. In particular, they are thin active-ingredient-containing, polymer-based films, which, when applied to a mucosa, in particular the oral mucosa, deliver the active ingredient directly into the mucosa. In one embodiment, the oral thin films are not sticky on the outside. In certain embodiments, the film product comprises multiple layers. In certain embodiments, the film product further comprises a protective layer.

The rich blood supply to the oral mucosa ensures a quick transfer of the active ingredient into the bloodstream. This delivery system has the advantage that the active ingredient is absorbed for the most part by the mucosa, and therefore avoided the first-pass metabolism. The active ingredient may be dissolved, emulsified or dispersed in the film. Suitable active ingredients may also be swallowed once the oral thin film has dissolved in the mouth, and thus may be absorbed via the gastrointestinal tract.

5.2 Polymers for Film Product

Water-soluble polymers comprise chemically very different natural or synthetic polymers, the common feature of which is their solubility in water or aqueous media. In certain embodiments, the polymers have a number of hydrophilic groups sufficient for the water-solubility and are not cross-linked. In certain embodiments, the hydrophilic groups may be non-ionic, anionic, cationic and/or zwitterionic. In certain embodiment, the at least one water-soluble polymer comprises polyvinyl alcohol, pullulan, polyethylene oxide and/or polyethylene glycol, and copolymers thereof. In certain embodiments, the polymers have the advantage that they are compatible with a large number of pharmaceutically active ingredients and are safe for treatment of a subject. Generally, any pharmaceutically active ingredient that is suitable for transmucosal or oral administration may be contained in the disclosed film product. In addition, conventional additives such as permeation enhancers, antioxidants, flavorings, taste-masking agents, preservatives, colorings, inert fillers, etc. may be contained in the film product.

In certain embodiments, the hydrophilic cellulosic polymer is in an amount ranging from about 5% to about 25% by weight (wt %), from about 25% to about 30% by weight (wt %), from about 30% to about 35% by weight (wt %), from about 35% to about 40% by weight (wt %), from about 40% to about 45% by weight (wt %), from about 45% to about 50% by weight (wt %), from about 50% to about 55% by weight (wt %), from about 55% to about 60% by weight (wt %), from about 60% to about 65% by weight (wt %), from about 65% to about 70% by weight (wt %), from about 70% to about 75% by weight (wt %), or from about 75% to about 80% by weight (wt %), from about 80% to about 85% by weight (wt %), relative to the total weight of the film product.

The polymer may be water soluble, water swellable, water insoluble, or a combination of one or more either water soluble, water swellable or water insoluble polymers. The polymer may include cellulose or a cellulose derivative. In certain embodiments, water soluble polymers include, but are not limited to, polyethylene oxide (PEO), pullulan, hydroxypropylmethyl cellulose (HPMC), hydroxyethyl cellulose (HPC), hydroxypropyl cellulose, polyvinyl pyrolidone, carboxymethyl cellulose, polyvinyl alcohol, sodium aginate, polyethylene glycol, xanthan gum, tragancanth gum, guar gum, acacia gum, arabic gum, polyacrylic acid, methylmethacrylate copolymer, carboxyvinyl copolymers, starch, gelatin, and combinations thereof. In certain embodiments, useful water insoluble polymers include, but are not limited to, ethyl cellulose, hydroxypropyl ethyl cellulose, cellulose acetate phthalate, hydroxypropyl methyl cellulose phthalate and combinations thereof.

As used herein the phrase "water soluble polymer" and variants thereof refer to a polymer that is at least partially soluble in water, and desirably fully or predominantly soluble in water, or absorbs water. Polymers that absorb water are often referred to as being water swellable polymers. The materials useful with the present invention may be water soluble or water swellable at room temperature and other temperatures, such as temperatures exceeding room temperature. Moreover, the materials may be water soluble or water swellable at pressures less than atmospheric pressure. Desirably, the water soluble polymers are water soluble or water swellable having at least 20 percent by weight water uptake. Water swellable polymers having a 25 or greater percent by weight water uptake are also useful. Films or dosage forms of the present invention formed from such water soluble polymers are desirably sufficiently water soluble to be dissolvable upon contact with bodily fluids.

Other polymers useful for incorporation into the film products include biodegradable polymers, copolymers, block polymers and combinations thereof. Among the known useful polymers or polymer classes which meet the above criteria are: poly(glycolic acid) (PGA), poly(lactic acid) (PLA), polydioxanoes, polyoxalates, poly(.alpha.-esters), polyanhydrides, polyacetates, polycaprolactones, poly (orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy) propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of polyurethane and poly(lactic acid), copolymers of .alpha.-amino acids, copolymers of .alpha.-amino acids and caproic acid, copolymers of .alpha.-benzyl glutamate and polyethylene glycol, copolymers of succinate and poly(glycols), polyphosphazene, polyhydroxy-alkanoates and mixtures thereof.

Other specific polymers useful include those marketed under the Medisorb and Biodel trademarks. The Medisorb materials are marketed by the Dupont Company of Wilmington, Del. and are generically identified as a "lactide/glycolide co-polymer" containing "propanoic acid, 2-hydroxy-polymer with hydroxy-polymer with hydroxyacetic acid." Four such polymers include lactide/glycolide 100 L, believed to be 100% lactide having a melting point within the range of 338-347° F. (170-1175° C.); lactide/glycolide 100 L, believed to be 100% glycolide having a melting point within the range of 437-455° F. (225-235° C.); lactide/glycolide 85/15, believed to be 85% lactide and 15% glycolide with a melting point within the range of 338-347° F. (170-175° C.); and lactide/glycolide 50/50, believed to be a copolymer of 50% lactide and 50% glycolide with a melting point within the range of 338-347° F. (170-175° C.).

Although a variety of different polymers may be used, it is desired to select polymers to provide a desired viscosity of the mixture prior to drying. For example, if the active or other components are not soluble in the selected solvent, a polymer that will provide a greater viscosity is desired to assist in maintaining uniformity. On the other hand, if the components are soluble in the solvent, a polymer that provides a lower viscosity may be preferred.

The polymer plays an important role in affecting the viscosity of the film. Viscosity is one property of a liquid that controls the stability of the active in an emulsion, a colloid or a suspension. Generally, the bulk material viscosity of the matrix will vary from about 4,000 cps to about 400,000 cps, from about 10,000 cps to about 100,000 cps, from about 30,000 cps to about 60,000 cps, and from about 60,000 cps to 80,000. The bulk material viscosity of the film-forming matrix will rapidly increase upon initiation of the drying process. In certain embodiments, K4M and K100M are used. In certain embodiments, the individual polymer viscosity is about 2,700-5,040 cps or about 75,000-140,000 cps.

The viscosity may be adjusted based on the selected pharmaceutically active agent depending on the other components within the matrix. For example, if the component is not soluble within the selected solvent, a proper viscosity may be selected to prevent the component from settling which would adversely affect the uniformity of the resulting film. The viscosity may be adjusted in different ways. To increase viscosity of the film matrix, the polymer may be chosen of a higher molecular weight or crosslinkers may be added, such as salts of calcium, sodium and potassium. The viscosity may also be adjusted by adjusting the temperature or by adding a viscosity increasing component. Components that will increase the viscosity or stabilize the emulsion/suspension include higher molecular weight polymers and polysaccharides and gums, which include without limitation, alginate, carrageenan, hydroxypropyl methyl cellulose, locust bean gum, guar gum, xanthan gum, dextran, gum arabic, gellan gum and combinations thereof.

It has also been observed that certain polymers which when used alone would ordinarily require a plasticizer to achieve a flexible film, can be combined without a plasticizer and yet achieve flexible films. For example, HPMC and HPC when used in combination provide a flexible, strong film with the appropriate plasticity and elasticity for manufacturing and storage. No additional plasticizer or polyalcohol is needed for flexibility.

Additionally, polyethylene oxide (PEO), when used alone or in combination with a hydrophilic cellulosic polymer, achieves flexible, strong films. Additional plasticizers or polyalcohols are not needed for flexibility. Non-limiting examples of suitable cellulosic polymers for combination with PEO include HPC and HPMC. PEO and HPC have essentially no gelation temperature, while HPMC has a gelation temperature of 58-64° C. (Methocel EF available from Dow Chemical Co.). Moreover, these films are sufficiently flexible even when substantially free of organic solvents, which may be removed without compromising film properties. As such, if there is no solvent present, then there is no plasticizer in the films. PEO based films also exhibit good resistance to tearing, little or no curling, and fast dissolution rates when the polymer component contains appropriate levels of PEO.

To achieve the desired film properties, the level and/or molecular weight of PEO in the polymer component may be varied. Modifying the PEO content affects properties such as tear resistance, dissolution rate, and adhesion tendencies. Thus, one method for controlling film properties is to modify the PEO content. For instance, in some embodiments rapid dissolving films are desirable. By modifying the content of the polymer component, the desired dissolution characteristics can be achieved.

In one embodiment, PEO ranges from about 0-5% by weight in the polymer component. In some embodiments, the amount of PEO desirably ranges from about 100 µg to about 950 µg. The hydrophilic cellulosic polymer ranges about 10-20%, 20-40%, 40-50%, 50-60%, 60-70%, 70-80%, 80-90%, 90% to about 95% by weight, or in a ratio of up to about 6:1 with the PEO. In certain embodiment, the ratio is not about 4:1 with the PEO.

In some embodiments, it may be desirable to vary the PEO levels to promote certain film properties. To obtain films with high tear resistance and desired dissolution rates, levels of no more than 5% of PEO in the polymer component are desirable. In certain embodiments, PEO levels of about less than 5% are desirable. In some embodiments, however, adhesion to the roof of the mouth may be desired, such as for administration to animals or children. In such cases, higher levels of PEO may be employed. More specifically, structural integrity and dissolution of the film can be controlled such that the film can adhere to mucosa and be readily removed, or adhere more firmly and be difficult to remove, depending on the intended use.

The molecular weight of the PEO may also be varied. High molecular weight PEO, such as about 4 million, may be desired to increase mucoadhesivity of the film. More desirably, the molecular weight may range from about 100,000 to 900,000, more desirably from about 100,000 to 600,000, and most desirably from about 100,000 to 300,000. In some embodiments, it may be desirable to combine high molecular weight (600,000 to 900,000) with low molecular weight (100,000 to 300,000) PEOs in the polymer component.

For instance, certain film properties may be attained by combining larger amount high molecular weight PEOs with smaller amounts of lower molecular weight PEOs. In certain embodiments, such compositions contain less than about 60% of the lower molecular weight PEO in the PEO-blend polymer component.

To balance the properties of adhesion prevention, target dissolution rate, and good tear resistance, desirable film compositions may include about less than 50% of low molecular weight PEO, optionally combined with a large amount of a low molecular weight PEO, with the remainder of the polymer component containing a hydrophilic cellulosic polymer (HPC or HPMC).

5.3 Controlled Release Films

The term "controlled release" is intended to mean the release of a pharmaceutically active agent at a pre-selected or desired rate. This rate will vary depending upon the application. Desirable rates include fast or immediate release profiles as well as delayed, sustained or sequential release. Combinations of release patterns, such as initial spiked release followed by lower levels of sustained release of active are contemplated. Pulsed drug releases are also contemplated.

The polymers that are chosen for the film products may also be chosen to allow for controlled disintegration of the pharmaceutically active agent. This may be achieved by providing a substantially water insoluble film that incorporates the pharmaceutically active agent that will be released from the film over time. This may be accomplished by incorporating a variety of different soluble or insoluble polymers and may also include biodegradable polymers in combination. Alternatively, coated controlled release active particles may be incorporated into a readily soluble film matrix to achieve the controlled release property of the active inside the digestive system upon consumption.

Films that provide a controlled release of the pharmaceutically active agent are particularly useful for buccal, gingival, sublingual and vaginal applications. The films disclosed herein are particularly useful where mucosal membranes or mucosal fluid is present due to their ability to readily wet and adhere to these areas.

The pharmaceutically active agent may be incorporated into the film in a controlled release form. For example, particles of drug may be coated with polymers such as ethyl cellulose or polymethacrylate, commercially available under brand names such as Aquacoat ECD and Eudragit E-100, respectively. Solutions of drug may also be absorbed on such polymer materials and incorporated into the film product. Other components such as fats and waxes, as well as sweeteners and/or flavors may also be employed in such controlled release film products.

5.4 Preparation of the Film Product

In one embodiment, the oral film disclosed herein is prepared according to the following method:

The ingredients of the disclosed compositions were combined by mixing until a uniform mixture is achieved. The compositions were then formed into a film by solvent vapor coating process. These films were then dried in an oven at 60-100° C. The films were dried to less than about 10% by weight water.

In one embodiment, the films is formed into a sheet prior to drying. After the desired components are combined to form a multi-component matrix, including the polymer, water, and the pharmaceutically active agent or other components as desired, the combination is formed into a sheet or film, by any method known in the art such as extrusion, coating, spreading, casting or drawing the multi-component matrix. If a multi-layered film is desired, this may be accomplished by co-extruding more than one combination of components which may be of the same or different composition. A multi-layered film may also be achieved by coating, spreading, or casting a combination onto an already formed film layer.

Although a variety of different film-forming techniques may be used, it is desirable to select a method that will provide a flexible film, such as reverse roll coating. The flexibility of the film allows for the sheets of film to be rolled and transported for storage or prior to being cut into individual dosage forms. Desirably, the films will also be self-supporting or in other words able to maintain their integrity and structure in the absence of a separate support. Furthermore, the films may be selected of materials that are edible or ingestible.

Coating or casting methods are particularly useful for the purpose of forming the films. Specific examples include reverse roll coating, gravure coating, immersion or dip coating, metering rod or meyer bar coating, slot die or extrusion coating, gap or knife over roll coating, air knife coating, curtain coating, or combinations thereof, especially when a multi-layered film is desired.

In one embodiment, the film product is prepared according to the following method:
Step A: A solution is prepared of at least one film-forming agent, optionally one crosslinking agent (such as, but not limited to, at least one polyethylene glycol), and at least one polar solvent (such as, but not limited to, alcohol, water, or the like; one solvent usable is ethanol). In one embodiment the film-forming agent can be any suitable alcohol-soluble polymer selected from the group consisting of polyvinylpyrrolidone (PVP), polyethylene glycol, or the like, or mixtures or combinations of one or more of the foregoing. In one embodiment, the film-forming agent can be any suitable water-soluble material, such as, but not limited to, albumin, gelatin, sugars, or the like, or mixtures or combinations of one or more of the foregoing. In one embodiment, the film-forming agent can be KOLLIDON.TM., a family of proprietary compositions containing PVP (available from BASF). The optional crosslinking agent can be one or more materials which crosslink in the presence of ultraviolet light. In one embodiment, the crosslinking agent can be polyethylene glycol diacrylate (PEGD) or other polyethylene glycol. The solvent can be alcohol or water.
Step B: To this solution is added either a suspension or solution of at least one pharmaceutically active agent in, for example, water, to form a mixture.
Step C: To the mixture of Step B is added optionally, a photo-initiator. Optionally, a surfactant can also be added.
Step D: the mixture of Step C is dried in an oven to form a film like sheet at pre-determined thickness and at pre-determined temperature.

5.5 Uses of the Film Product

The thin films comprising the polymers allow for a range of disintegration times for the films. A variation or extension in the time over which a film will disintegrate may achieve control over the rate that the pharmaceutically active agent is released, which may allow for a sustained release delivery system. In addition, the films may be used for the administration of an active to any of several body surfaces, especially those including mucous membranes, such as oral, anal, vaginal, opthalmological, the surface of a wound, either on a skin surface or within a body such as during surgery, and similar surfaces. The films may be used to orally administer a pharmaceutically active agent. This is accomplished by preparing the films as described above and introducing them to the oral cavity of a mammal. This film may be prepared and adhered to a second or support layer from which it is removed prior to use, i.e. introduction to the oral cavity. An adhesive may be used to attach the film to the support or backing material. If an adhesive is used, it will desirably be a food grade adhesive that is ingestible and does not alter the properties of the pharmaceutically active agent. Mucoadhesive compositions are particularly useful.

The films may be applied under or to the tongue of the mammal. When this is desired, a specific film shape, corresponding to the shape of the tongue may be preferred. Therefore, the film may be cut to a shape where the side of the film corresponding to the back of the tongue will be longer than the side corresponding to the front of the tongue. Desirably, the film will adhere to the oral cavity preventing it from being ejected from the oral cavity and permitting more of the active to be introduced to the oral cavity as the film dissolves.

Another use for the films takes advantage of the films to dissolve quickly when introduce to a liquid. A pharmaceutically active agent may be introduced to a liquid by preparing a film, introducing it to a liquid, and allowing it to dissolve. This may be used either to prepare a liquid dosage form of an active, or to flavor a beverage.

The films are desirably packaged in sealed, air and moisture resistant packages to protect the active from exposure oxidation, hydrolysis, volatilization and interaction with the environment. In one embodiment, a series of such unit doses are packaged together in accordance with the prescribed regimen or treatment, e.g., a 10-90 day supply, depending on the particular therapy. The individual films can be packaged on a backing and peeled off for use.

5.6 Conditions to be Treated

The present disclosure provides methods and film product for treating or preventing thrombosis. In certain embodiments, the disclosure provides methods and compositions for treating or preventing left ventricular thrombus, atrial fibrillation, acute coronary syndrome, reduce the risk of stroke and systemic embolism. In one embodiment, the methods and compositions provide treatment of subjects with nonvalvular atrial fibrillation. In certain embodiments, the methods and compositions provide prophylaxis of deep vein thrombosis, which may lead to pulmonary embolism. In certain embodiments, the subject has undergone surgery. In certain embodiments, the methods and composition reduce the risk of recurrent deep vein thrombosis and pulmonary embolism following initial therapy.

5.7 Combination with Other Active Agents

The present film product containing the active agent (e.g., apixaban, or a pharmaceutically acceptable salt, derivative, or solvate thereof) or composition may be administered (or applied) to the subject simultaneously with, before, after, or in a sequence and within a time interval of, the administration of a second active agent(s).

By co-administration it is meant either the administration of a single film product containing both the present agent (e.g., apixaban, or a pharmaceutically acceptable salt, derivative, or solvate thereof) and a second active agent(s), or the administration of the present agent and a second active agent(s) as separate film product within short time periods.

The present film product can be combined and administered with a second active agent(s) in separate film product. In certain embodiments, the separate film products are administered simultaneously. In certain embodiments, the separate film products are not administered simultaneously, such as, for example, in a sequential manner.

The present film product may be administered (or applied) to a subject alone, or may be administered (or applied) to a subject in combination with one or more other treatments/agents (a second agent).

In certain embodiments, the second agent is an agent in the treatment of thrombosis or related disorders.

In certain embodiments, combination therapy means simultaneous administration of the compounds in the same film product, simultaneous administration of the compounds in separate film products, or separate administration of the film products (in separate film products).

In certain embodiments, the second agent/treatment is used as adjunctive therapy to the present film product or composition. In certain embodiments, the treatment includes a phase wherein treatment with the second agent/treatment takes place after treatment with the present film product has ceased. In certain embodiments, the treatment includes a phase where treatment with the present film product and treatment with the second agent/treatment overlap.

Combination therapy can be sequential or can be administered simultaneously. In either case, these drugs and/or therapies are said to be "co-administered." It is to be understood that "co-administered" does not necessarily mean that the drugs and/or therapies are administered in a combined form (i.e., they may be administered separately (e.g., as separate compositions or formulations) or together (e.g., in the same formulation or composition) to the same or different sites at the same or different times).

In certain embodiments, a subject is treated concurrently (or concomitantly) with the present film product and a second agent. In certain embodiments, a subject is treated initially with the present film product, followed by cessation of the present film product treatment and initiation of treatment with a second agent. In certain embodiments, the present film product is used as an initial treatment, e.g., by administration of one, two or three doses, and a second agent is administered to prolong the effect of the present film product, or alternatively, to boost the effect of the present film product. A person of ordinary skill in the art will recognize that other variations of the presented schemes are possible, e.g., initiating treatment of a subject with the present film product, followed by a period wherein the subject is treated with a second agent as adjunct therapy to the present film product treatment, followed by cessation of the present film product treatment.

The present compound and the other pharmaceutically active agent(s) may be administered together or separately and, when administered separately this may occur simultaneously or sequentially in any order. The amounts of the present pharmaceutically active agent and the other pharmaceutically active agent(s) and the relative timings of administration will be selected in order to achieve the desired combined therapeutic effect.

In various embodiments, the therapies (e.g., an film product provided herein and a second agent in a combination therapy) are administered about 0 minutes to about 5 minutes apart, about 5 minutes to about 30 minutes apart, about 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart. In certain embodiments, the therapies are administered no more than 12 hours apart or no more than 24 hours apart.

The second agent can act additively or synergistically with the present pharmaceutically active ingredient. In one embodiment, the film product provided herein is administered concurrently with one or more second agents in the same film product. In another embodiment, a film product provided herein is administered concurrently with one or more second agents in separate film product. In still another embodiment, a film product provided herein is administered prior to or subsequent to administration of a second agent. Also contemplated are administration of a film product provided herein and a second agent by the same or different routes of administration, e.g., oral and parenteral.

5.8 Dosing

The present film product may be administered (or applied) once, twice, three times, four times, five times, six times or more per day, or as needed, during the course of treatment. In certain embodiments, the present film product may be administered at least once a day, at least twice a day, at least three times per day, or more. In certain embodiments, the present film product may be administered at least once a week, at least twice a week, at least three times a week, at least once per month, at least twice per month, or more frequently. Treatment can continue as long as needed. In one embodiment, the film product may be administered (or applied) to a subject once daily.

The present film product may be administered (or applied) daily, weekly, biweekly, several times daily, semi-weekly, every other day, bi-weekly, quarterly, several times per week, semi-weekly, monthly etc., to maintain an effective dosage level. The duration and frequency of treatment may depend upon the subject's response to treatment.

In certain embodiments, a subject may be administered 1 dose, 2 doses, 3 doses, 4 doses, 5 doses, 6 doses or more of the film product. In certain embodiments, a single dose of the present film product is administered in the present method. In certain embodiments, multiple doses of the present film product (e.g., 2 doses, 3 doses, 4 doses, 5 doses, 6 doses, 7 doses, 8 doses, 9 doses, 10 doses or more) are administered in the present method. In one embodiment, each dose equates to a single film product.

In certain embodiments, the administration of the present film product is continued over a period of up to 2 days, up to 3 days, up to 4 days, up to 5 days, up to 6 days, up to 1 week, up to 2 weeks, up to 3 weeks, up to 4 weeks, 2 weeks, 3 weeks, 4 weeks, 5 weeks, 6 weeks, 7 weeks, 8 weeks, 9 weeks, 10 weeks, or longer.

In certain embodiments, the present film product is administered once, twice, at least twice, at least three times, at least four times, at least five time, at least six times, at least seven times, at least eight times, at least nine times, or more per treatment.

5.9 Subjects

The subject may be a human. In certain embodiments, the subject is a non-human animal. The non-human animal may be a mammal selected from the group consisting of primates (non-human primates), pigs, rodents, or rabbits. In an embodiment, the subject is a pig, such as a miniswine. In another embodiment, the subject is a mouse.

5.10 Kits

The present disclosure also encompasses an article of manufacture, e.g., a kit. The article of manufacture may contain the present film product in a suitable container with labeling and instructions for use. Optionally, an applicator can be provided in or attached to the container, or separately from the container.

Instructions may be packaged with the film product, for example, a pamphlet or package label. The labeling instructions explain how to the present film product, in an amount and for a period of time sufficient to treat or prevent the disorder or condition discussed herein. In certain embodiments, the label includes the dosage and administration instructions, the film product, the clinical pharmacology, drug resistance, pharmacokinetics, absorption, bioavailability, and/or contraindications.

This invention will be better understood from the following examples. However, one skilled in the art will readily appreciate that the specific methods and results discussed are merely illustrative and not limiting.

6. EXAMPLES

Example 6.1

Film Production:
The ingredients of inventive compositions in the following tables were combined by mixing until a uniform mixture was achieved. The compositions were then formed into a film by solvent vapor coating process. These films were then dried in an oven at the temperature at approximately 80-120° C. The films were dried to less than about 10% by weight water. The films were flexible, self-supporting and provided a uniform distribution of the components within the film.

6.2 Dissolution Study

Formulations according to this invention, when dissolution tested in vitro preferably exhibit the following dissolution criteria. The dissolution test is performed in 900 mL of 0.05 M sodium phosphate pH 6.8 with 0.05% sodium lauryl sulfate solution as dissolution medium at 37° C., using USP Apparatus 2 (paddles) method at a rotation speed of 75 rpm. Samples are removed according to pre-determined time points and analyzed for apixaban by HPLC at 280 nm. Table 1 and 2 show apixaban oral film composition prepared using the solvent vapor coating process that were evaluated in the dissolution study.

TABLE 1

| Ingredient | Composition wt/wt % | | | | | |
|---|---|---|---|---|---|---|
|  | Ex 1 | Ex 2 | Ex 3 | Ex 4 | Ex 5 | Ex 6 |
| apixaban | 10 | 10 | 10 | 10 | 10 | 10 |
| HPMC E50 | 10 | — | — | — | — | 5 |
| HPMC E15 | 50 | — | — |  |  |  |
| HPMC K100LV |  |  |  | — | — | 5 |
| POLYOX™ N60K | — | 10 | — | — | 10 | — |
| POLYOX™ N10 | — | — | 35 | 35 | 40 | 45 |
| POLYOX™ N80 | — | 40 | 35 | 35 | — | — |
| PEG 6000 | 20 | 20 | 20 | 10 | 20 | 20 |
| Maltose | — | 20 | — | — | — | 15 |
| CMC-L7 |  |  |  | 10 | 20 | 5 |
| Starch | 10 | — | — | — | — | — |

TABLE 2

| Ingredient | Composition wt/wt % | | |
|---|---|---|---|
|  | Ex 7 | Ex 8 | Ex 9 |
| Apixaban | 10 | 10 | 10 |
| HPMC K4M |  | 15 | 15 |
| HPMC K100M | 10 | — |  |
| HPMC E50 |  |  | 15 |
| HPMC E15 | 5 | 20 |  |
| Polyethylene glycol 6000 | 20 | 20 | 20 |
| Maltose | 25 | 25 | 25 |
| Starch | 20 | — |  |
| Glycerin | 10 | 10 |  |
| Propylene glycol |  |  | 10 |
| Mint Flavor |  |  | 2 |
| Strawberry Flavor |  |  | 3 |
| Titanium dioxide |  |  | 1 |
| % release at 30 minutes time point | 50.9 | 65.91 | 55.70 |

Table 3 and 4 show the time course of the dissolution data of Example 7 and 8 when place in 25±2° C./75±5% RH and 40±2° C./75±5% RH for 1 month.

TABLE 3

| Dissolution Studies Ex 7 Test Interval | Initial | 1 month | |
|---|---|---|---|
| | | Long Term Stability Studies: 25 ± 2° C./75 ± 5% RH | Accelerated Stability Studies: 40 ± 2° C./75 ± 5% RH |
| 5 min | 4.33 | 3.58 | 3.47 |
| 10 min | 12.36 | 12.16 | 13.17 |
| 20 min | 31.81 | 62.15 | 42.17 |
| 30 min | 51.32 | 62.15 | 78.19 |
| 45 min | 79.68 | 89.48 | 98.81 |
| 60 min | 92.66 | 97.15 | 101.43 |

TABLE 4

| Dissolution Studies Ex 8 Test Interval | Initial | 1 month | |
|---|---|---|---|
| | | Long Term Stability Studies: 25 ± 2° C./75 ± 5% RH | Accelerated Stability Studies: 40 ± 2° C./75 ± 5% RH |
| 5 min | 4.49 | 2.46 | 2.76 |
| 10 min | 12.98 | 9.45 | 10.60 |
| 20 min | 37.55 | 35.83 | 37.68 |
| 30 min | 66.10 | 73.37 | 69.91 |
| 45 min | 83.12 | 97.77 | 90.32 |
| 60 min | 89.57 | 99.51 | 97.20 |

Table 5 and 6 show the water content and disintegration time of Example 7 and 8 when place in 25±2° C./75±5% RH and 40±2° C./75±5% RH for 1 month.

TABLE 5

| Water Content | Initial | 1 Month | |
|---|---|---|---|
| | | Long Term Stability Studies: 25 ± 2° C./75 ± 5% RH | Accelerated Stability Studies: 40 ± 2° C./75 ± 5% RH |
| Ex 7 | 6.01 | 8.41 | 8.72 |
| Ex 8 | 7.23 | 9.13 | 8.46 |

TABLE 6

| Disintegration Time | Initial (second) | 1 Month | |
|---|---|---|---|
| | | Long Term Stability Studies: 25 ± 2° C./75 ± 5% RH | Accelerated Stability Studies: 40 ± 2° C./75 ± 5% RH |
| Ex 7 | 120 | 120 | 155 |
| Ex 8 | 120 | 120 | 155 |

6.3 Disintegration

The disintegration was determined using a disintegrator. Distilled Water at a temperature of 37±2° C. was used as the test media. The films were subjected at successive vertical immersion and the time until total disintegration was recorded.

An accelerated and long-term stability studies was conducted to determine the stability of the oral film

6.4 Film Thickness

Micrometer screw (Mitutoyo, Neuss, Germany) was used to determine film thicknesses of oral film samples.

6.5 Swelling Test Study

To mimic oral film oral disintegrating phenomenon, a swelling test study has carried out. An oral film of 20×20 mm$^2$ was weighed and kept in a Petri dish. A 10 ml of distilled water at 37° C. was added into the Petri dish and covered with its lid. Time was measured to determine when it will fully disintegrated.

Disintegration agents are therefore added to the formulation, which promote the breakup of the tablets into small granules and their constituent particles and thus enable a faster liberation of the drug particles from the tablet matrix leading to an increase in surface area for subsequent dissolution. In doing so, the surface area available for dissolution is increased and drug dissolution is accelerated [1].

As an orally disintegrating film, the controlling of the oral film's disintegration properties is important since it needs to be fast disintegrated in the mouth. Therefore, different disintegration agents (disintegrates) were evaluated. In the examples below, it shows the swelling time has improved with the addition of disintegrants (sodium starch glycolate, Crosprovidone XL, Crosprovidone XL-10, sodium starch glycolate); however, the release of the active ingredient at 30 minutes time point reminds lower than 80%. As shown in Table 7, adding the disintegrate did not improve the release profile but it reduced the swelling time.

TABLE 7

| | Composition wt/wt % | | | | | |
|---|---|---|---|---|---|---|
| Ingredients | Ex 8 | Ex 10 | Ex 11 | Ex 12 | Ex 13 | Ex 14 |
| Apixaban | 10 | 10 | 10 | 10 | 10 | 10 |
| HPMC K4M | 15 | 12.5 | 15 | 15 | 14 | 16 |
| HPMC E50 | | 15 | 15 | 15 | 15 | 15 |
| HPMC E15 | 20 | | | | | |
| Polyethylene glycol 6000 | 20 | 25 | 25 | 25 | 25 | 25 |
| Maltose | 25 | 12.5 | 10 | 10 | 15 | 17.5 |
| Glycerin | 10 | 9 | 9 | 9 | 9 | 9 |
| CMC-7MF | — | 10 | — | — | 4 | |
| sodium starch glycolate | — | | | | | 1.5 |
| Crosprovidone XL | — | | 10 | — | 2 | |
| Crosprovidone XL-10 | — | | | 10 | | |
| Mint Flavor | — | 2 | 2 | 2 | 2 | 2 |
| Strawberry Flavor | — | 3 | 3 | 3 | 3 | 3 |
| Titanium dioxide | — | 1 | 1 | 1 | 1 | 1 |
| Film Swelling time (min) | >30 | 3 | <5 | <5 | 2-10 | 5-10 |
| % release at 30 minutes time point | 65.91 | 44.41 | 29.67 | 28.31 | 61.83 | 65.61 |

6.6 Use of Lower Molecular HPMC with Eudragit Polymers

When using lower molecular weight of HPMC such as HPMC L100 LV, it improves the dissolution rate (Ex 8 vs. Ex15).

Table 8 provides the physical property of different HPMC grade.

TABLE 8

| HPMC Grade | Viscosity at 2% solution (CPS)[a] | Weight Average Molecular Weight[a] |
|---|---|---|
| HPMC K4M | 2700-5040 | 400,000 |
| HPMC K100 LV | 80-120 | 164,000 |
| HPMC E50 | 40-60 | 91,300 |
| HPMC E15 | 12-18 | 52,000 |

[a]: Ashland- from matrix to film coating, your full-service pharmaceutical technology resource It was observed that with lower molecular weight of HPMC but in combination with Eudragit RL PO, the dissolution profile will reduce (Example 15 vs. 16) as shown in Table 9. The same phenomena is also observed for HPMC with different Eudragit polymers. Eudragit E PO is used as immediate release while, Eudragit NM 30 D and Eudragit RL PO are used as time controlled release. The disintegration time of the oral film in Example 17 to 19 of Table 10 were within 2 minutes; however, their % release reminds slow.

TABLE 9

| | Composition wt/wt % | | |
|---|---|---|---|
| Ingredient | Ex 8 | Ex 15 | Ex 16 |
| Apixaban | 10 | 8 | 10 |
| HPMC K4M | 15 | | |
| HPMC K100LV | | 30 | 20 |
| HPMC E15 | 20 | | |
| Eudragit RL PO | — | — | 4 |
| Polyethylene glycol 6000 | 20 | 12 | 24 |
| Polyethylene glycol 20000 | | 12 | |
| Maltose | 25 | 21 | 31 |
| CMC-L7 | | | |
| Glycerin | 10 | 11 | 5 |
| Mint Flavor | | 2 | 2 |
| Strawberry Flavor | | 3 | 3 |
| Titanium dioxide | | 1 | 1 |
| % release at 30 minutes time point | 65.91 | 108.85 | 82.07 |

TABLE 10

| | Composition wt/wt % | | |
|---|---|---|---|
| Ingredients | Ex 17 | Ex 18 | Ex19 |
| Apixaban | 10 | 10 | 10 |
| HPMC E50 | 30 | 30 | 30 |
| Eudragit E PO | 10 | | |
| Eudragit NM 30 D | — | 3 | — |
| Eudragit RL PO | — | — | 4 |
| Polyethylene glycol 6000 | 17.5 | 24 | 24 |
| Maltose | 17.5 | 22 | 21 |
| Glycerin | 5 | 5 | 5 |
| Mint Flavor | 6 | 2 | 2 |
| Strawberry Flavor | 3 | 3 | 3 |
| Titanium dioxide | 1 | 1 | 1 |
| Disintegration Time (seconds) | ~20 | ~49 | ~49 |
| % release at 30 minutes time point | 68.88 | 73.95 | 8.65 |

In Table 11, it was observed that with lower molecular weight of HPMC but in combination with Eudragit polymer and Carbomer, the dissolution profile will further reduce even though the disintegration time reminds similar.

TABLE 11

| | Composition wt/wt % | | | | |
|---|---|---|---|---|---|
| Ingredients | Ex 19 | Ex 20 | Ex 18 | Ex 21 | Ex 22 |
| Apixaban | 10 | 10 | 10 | 10 | 10 |
| HPMC E50 | 30 | 30 | 30 | 30 | 30 |
| Eudragit RL PO | 4 | 3 | | | |
| Eudragit NM 30 D | | | 3 | 8 | 8 |
| Carbomer 934 | | 2 | | 4 | 6 |
| Polyethylene glycol 6000 | 24 | 20 | 24 | 16 | 15 |
| Maltose | 21 | 24 | 22 | 16 | 15 |
| Glycerin | 5 | 5 | 5 | 5 | 5 |
| Sucralose | | | | 1 | 1 |
| Mint Flavor | 2 | 2 | 2 | 6 | 6 |
| Strawberry Flavor | 3 | 3 | 3 | 3 | 3 |
| Titanium dioxide | 1 | 1 | 1 | 1 | 1 |
| Disintegration Time (seconds) | ~49 | ~45 | ~49 | ~58 | ~75 |
| % release at 30 minutes time point | 68.88 | 31.84 | 73.95 | 59.42 | 21.58 |

6.7 Stability Study

A long-term (25±2° C./75±5% RH) stability studies was conducted to determine the stability of the oral film, the data are shown in Table 12 to Table 15. From the example 7 to 9 and Example 22, the oral film reminds stable under the room temperature for more than 3 months, no significant changes in terms of assay, impurity, water content, disintegration time and % release at 30 minutes time points

TABLE 12

Long term stability study on Example 7

| Test Interval | Assay | Apixaban Impurity C | Total Impurities | Water Content | Disintegration time (second) | % release at 30 minutes |
|---|---|---|---|---|---|---|
| Initial | 100.88 | 0.03 | 0.03 | 6.01 | 120 | 50.90 |
| 1 month | 103.04 | 0.04 | 0.04 | 8.41 | 120 | 62.94 |
| 3 month | 105.19 | 0.04 | 0.04 | 8.45 | 55.3 | 63.7 |

TABLE 13

Long term stability study on Example 8

| Test Interval | Assay (%) | Apixaban Impurity C (%) | Total Impurities (%) | Water Content (%) | Disintegration time (second) | % release at 30 minutes |
|---|---|---|---|---|---|---|
| Initial | 99.49 | 0.04 | 0.04 | 7.23 | 120 | 65.91 |
| 1 month | 100.84 | 0.03 | 0.03 | 9.13 | 120 | 71.69 |
| 3 month | 101.65 | 0.03 | 0.03 | 7.68 | 76.7 | 70.97 |

TABLE 14

Long term stability study on Example 9

| Test Interval | Assay (%) | Apixaban Impurity C (%) | Unknown Impurity at 21.59 min (%) | Total Impurities (%) | Water Content (%) | Disintegration time (second) | % release at 30 minutes |
|---|---|---|---|---|---|---|---|
| Initial | 104.79 | 0.03 | — | 0.03 | 8.03 | 106.67 | 55.7 |
| 3 month | 105.10 | 0.04 | 0.02 | 0.05 | 7.1 | 71.33 | 50.97 |

TABLE 15

Long term stability study on Example 22

| Test Interval | Assay (%) | Unknown Impurity at 9.87 min (%) | Apixaban Impurity C (%) | Total Impurities (%) | Water Content (%) | Disintegration time (second) | % release at 30 minutes |
|---|---|---|---|---|---|---|---|
| Initial | 105.66 | — | 0.02 | 0.02 | 5.46 | 75 | 21.58 |
| 1 month | 107.05 | 0.01 | 0.03 | 0.05 | 4.36 | 90 | 14.7 |
| 3 month | 108.51 | 0.02 | 0.03 | 0.05 | 4.96 | 101 | 17.47 |

Exemplary Products, Systems and Methods are Set Out in the Following Items:

1. A water-soluble film product comprising: (i) apixaban or a pharmaceutically acceptable salt thereof; and (ii) a water-soluble polymer comprising a hydrophilic cellulosic polymer wherein the water-soluble polymer comprises at least 10% hydrophilic cellulosic polymer,
   (i) less than 77 wt % of apixaban or a pharmaceutically acceptable salt thereof dissolves within 30 minutes in a pH 6.8 phosphate buffer containing 0.05% sodium lauryl sulfate,
   (ii) the film comprises less than 10% of water content, and
   (iii) the disintegration time of the film is less than 5 minutes.
2. A water-soluble film product comprising: (i) apixaban or a pharmaceutically acceptable salt thereof; and (ii) a water-soluble polymer comprising a hydrophilic cellulosic polymer wherein:
   (i) the water-soluble polymer comprises at least 10% hydrophilic cellulosic polymer and less than 5% of polyethylene oxide,
   (ii) less than 77 wt % of apixaban or a pharmaceutically acceptable salt thereof dissolves within 30 minutes in a pH 6.8 phosphate buffer containing 0.05% sodium lauryl sulfate,
   (iii) the film comprises less than 10% of water content, and
   (iv) the disintegration time of the film is less than 5 minutes.
3. The water-soluble film of anyone of the preceding items wherein the apixaban is crystalline.
4. The water-soluble film of anyone of the preceding items wherein less than 77% of apixaban dissolves within 30 minutes in a pH 6.8 phosphate buffer containing 0.05% sodium lauryl sulfate.
5. The water-soluble film of anyone of the preceding items comprising 8-12% wt/wt % of apixaban.
6. The water-soluble film of anyone of the preceding items comprising 10% wt/wt % of apixaban.
7. The water-soluble film of anyone of the preceding items wherein the hydrophilic cellulosic polymer is HPMC or carboxymethyl cellulose ("CMC") polymer.
8. The water-soluble film of anyone of the preceding items wherein the HPMC is HPMC 3, HPMC E5, HPMC E6, HPMC E15, HPMC E50, HPMC 5FM, HPMC E10M, HPMC K 250 PH, HPMC K 750 PH, HPMC K1500PH, HPMC K4M, HPMC K15M K35M, HPMC K100M, HPMC K200M or a combination thereof.
9. The water-soluble film of anyone of the preceding items further comprising PEG, maltose, starch, glycerin, water soluble resins, or a combination thereof.

10. The water-soluble film of anyone of the preceding items wherein the PEG is PEG 6000.

11. The water-soluble film anyone of the preceding items, wherein said film has a bulk material viscosity of 10,000 cps to 100,000 cps 12. The water-soluble film anyone of the preceding items, wherein said film has a thickness of 2 mils to 9 mils.

13. The water-soluble film anyone of the preceding items, further comprising an additional pharmaceutical active ingredient.

14. The water-soluble film anyone of the preceding items, further comprising one or more sweeteners.

15. The water-soluble film anyone of the preceding items, further comprising one or more flavors.

16. The water-soluble film of item 1 or 2, further comprising an anticoagulant.

17. A method for treating thrombosis or a related disorder comprising the step of applying the film product anyone of the preceding items to a human subject in need thereof.

18. The method of anyone of the preceding items wherein about 0.5 mg to about 20 mg of apixaban is delivered from the film product to the human subject.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, and publications are cited throughout this application, the disclosures of which, particularly, including all disclosed chemical structures, are incorporated herein by reference. Citation of the above publications or documents is not intended as an admission that any of the foregoing is pertinent prior art, nor does it constitute any admission as to the contents or date of these publications or documents. All references cited herein are incorporated by reference to the same extent as if each individual publication, patent application, or patent, was specifically and individually indicated to be incorporated by reference.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

What is claimed is:

1. A method for treating thrombosis or a related disorder comprising the step of applying a film product to a human subject in need thereof,
   wherein the film product is an immediate release oral water-soluble film, the film comprising: (i) apixaban or a pharmaceutically acceptable salt thereof; and (ii) a water-soluble polymer comprising a hydrophilic cellulosic polymer wherein the water-soluble polymer comprises 10%-50% by weight of a hydrophilic cellulosic polymer selected from the group consisting of hydroxypropylmethyl cellulose (HPMC), hydroxyethyl cellulose (HEC), hydroxypropylcellulose (HPC) and carboxymethyl cellulose (CMC) polymer,
   wherein:
   (i) the immediate release oral water-soluble film exhibits an initial rate-controlled release profile according to which less than 77 wt % of apixaban or a pharmaceutically acceptable salt thereof dissolves within 30 minutes in a pH 6.8 phosphate buffer containing 0.05% sodium lauryl sulfate,
   (ii) the film comprises 1% to 10% of water content, and
   (iii) the disintegration time of the film is less than 5 minutes.

2. The method of claim 1 wherein about 0.5 mg to about 20 mg of apixaban is delivered from the film product to the human subject.

3. The method of claim 1, wherein about 10-60 wt % of apixaban or a pharmaceutically acceptable salt thereof dissolves within about 30 minutes in a pH 6.8 phosphate buffer containing 0.05% sodium lauryl sulfate.

4. The method of claim 1, wherein the film comprises 3% to 8% of water content.

5. The method of claim 1, wherein the disintegration time of the film is less than 2 minutes.

6. The method of claim 1, wherein the hydrophilic cellulosic polymer is present at about 25-40% by weight.

7. The method of claim 1, wherein the film further comprises polyethylene oxide at a concentration of no more than 5% by weight.

8. The method of claim 1, wherein the film further comprises one or more of polyethylene glycol (PEG), maltose, starch, glycerin, or water soluble resins.

9. The method of claim 1, wherein the film further comprises or more of a sweetener, flavor, or anticoagulant.

10. The method of claim 1, wherein the film further comprises a polymer selected from the group consisting of polymethacrylate and polyacrylic acid.

* * * * *